United States Patent [19]

McCuiston

[11] Patent Number: 5,074,315
[45] Date of Patent: Dec. 24, 1991

[54] ARTIFICIAL FORESKIN DEVICE

[76] Inventor: James J. McCuiston, P.O. Box 160, Gerry Dr., Kernersville, N.C. 27284

[21] Appl. No.: 609,183

[22] Filed: Nov. 2, 1990

[51] Int. Cl.$^5$ .............................. A61F 6/04; A61F 5/00
[52] U.S. Cl. ...................................... 128/844; 128/79; 128/918
[58] Field of Search ................. 128/842, 844, 79, 918, 128/80 C, 166; 604/347-353, 330

[56] References Cited

U.S. PATENT DOCUMENTS

| 27,065 | 4/1897 | Scheinkman | 128/79 |
|---|---|---|---|
| 2,538,136 | 1/1951 | Twachtman | 128/79 |
| 2,705,951 | 4/1955 | Crowner | 128/79 |
| 3,074,400 | 1/1963 | Schulman | 128/165 |
| 3,153,413 | 10/1964 | Gottfried | 128/165 |
| 3,621,840 | 11/1971 | Macchion | 128/79 |
| 3,648,291 | 3/1972 | Pankers | 128/165 |
| 3,893,455 | 7/1975 | McNally | 128/79 |
| 4,240,413 | 12/1980 | Hanus | 128/79 |
| 4,263,914 | 4/1981 | Pawlak | 128/79 |
| 4,820,290 | 4/1989 | Yahr | 604/349 |

Primary Examiner—Robert A. Hafer
Assistant Examiner—Michael Brown
Attorney, Agent, or Firm—Rhodes, Coats & Bennett

[57] ABSTRACT

A prophylactic device adapted to be worn on a penis. The device includes a bottle-shaped, tubular sheath open at both ends and an elastic band attached along one of the ends of the sheath for securing the sheath to the glans of the penis. The tubular sheath is operable to prevent constant contact between clothing and the glans of the penis while, at the same time, permitting normal micturition functions. The band is relatively thick and wide to form a roll-preventing perimeter and further includes raised, generally longitudinally extending ribs arranged about the outer surface of the band for preventing the band from rolling up. In an alternative embodiment, the sheath includes an inner layer and an outer layer defining a region therebetween for receiving a tactile preventing substance. This region may include a series of parallel baffles along its inner surface for slowing the flow of the tactile preventing liquid.

12 Claims, 1 Drawing Sheet

ARTIFICIAL FORESKIN DEVICE

BACKGROUND OF THE INVENTION (2) Field of the Invention

The present invention relates generally to prophylactic-type devices and, more particularly, to a device designed to fit over and protect the glans penis from constant contact with clothing, thereby improving the sensitivity of the penis during sexual intercourse.

(2) Description of the Prior Art

It is the practice in much of the world to remove the foreskin from the glans penis of a child at birth or shortly thereafter. In some cases this is for religious reasons but in the majority of cases it is to reduce the likelihood that the child will later contract an infection for failure to keep the area between the foreskin and corona clean. Some children are not circumcised at birth and only later as young adults have the foreskin removed because of health, social, or other requirements such as military service. Since the head of the penis has been protected by the foreskin up until that time, a considerable period of time may be necessary for the person to adjust to the increased sensitivity now occasioned by the removal of the foreskin. A noticeable decrease in sensitivity during sexual intercourse occurs as the head of the penis becomes assimilated to constant contact with clothing.

Conventional prophylactic devices are designed to protect a tumescent penis from sexually transmitted diseases while retaining the ejaculate to eliminate or reduce the chance of an unwanted pregnancy. Prior art devices generally extend the length of the penis, however some devices featured an abbreviated hood for encasing only the glans penis. One such device is disclosed in U.S. Pat. No. 4,820,290, issued to Yahr.

These types of devices are generally not designed for use on a flaccid penis although the device taught by Yahr is better suited for that purpose than more conventional roll-type condoms. In addition, such devices are worn only during sexual intercourse and are specifically directed to being almost undetectable when worn.

Thus, there remains a need for a new and improved prophylactic device which is operable to protect the head of the penis from constant contact with clothing, thereby permitting the original sensitivity of the head of the penis to be regained over a period of time. In addition, the device should permit normal micturition functions without the necessity of removing the device.

SUMMARY OF THE INVENTION

The present invention is directed to a prophylactic device which is adapted to be worn on a penis. The device includes a bottle-shaped, tubular sheath open at both ends and an elastic band attached along one of the ends of the sheath for securing the sheath to the glans of the penis. The tubular sheath is operable to prevent constant contact between clothing and the glans of the penis while, at the same time, permitting normal micturition functions. The band is relatively thick and wide to form a roll-preventing perimeter and further includes raised, generally longitudinally extending ribs arranged about the outer surface of the band for preventing the band from rolling up. In an alternative embodiment, the sheath includes an inner layer and an outer layer defining a region therebetween for receiving a tactile preventing substance. This region may include a series of parallel baffles along its inner surface for slowing the flow of the tactile preventing liquid.

Accordingly, one aspect of the present invention is to provide a prophylactic device worn on a penis. The device includes a tubular sheath open at both ends and an elastic band attached along one of the ends of the sheath. The sheath and the band are constructed and sized to adapt to the distal end of the penis with the sheath covering the glans of the penis and the band seating around the coronal sulcus of the penis to secure the device in position upon the penis, whereby the tubular sheath is operable to prevent contact between clothing and the glans of the penis while, at the same time, permitting normal micturition functions.

Another aspect of the present invention is to provide a prophylactic device worn on a penis. The device includes a tubular sheath open at both ends. The sheath has an inner layer and an outer layer defining a region therebetween for receiving a tactile preventing substance. An elastic band is attached along one of the ends of the sheath. The sheath and the band are constructed and sized to adapt to the distal end of the penis with the sheath covering the glans of the penis an the band seating around the coronal sulcus of the penis to secure the device in position upon the penis, whereby the tubular sheath is operable to prevent contact between clothing and the glans of the penis while, at the same time, permitting normal micturition functions.

These and other aspects of the present invention will become apparent to those skilled in the art after a reading of the following description of the preferred embodiment when considered with the drawings.

DESCRIPTION OF THE PREFERRED EMBODIMENTS

In the following description, like references characters designate like or corresponding parts throughout the several views. Also in the following description, it is to be understood that such terms as "forward", "rearward", "left", "right", "upwardly", "downwardly", and the like are words of convenience and are not to be construed as limiting terms.

Figure 1:
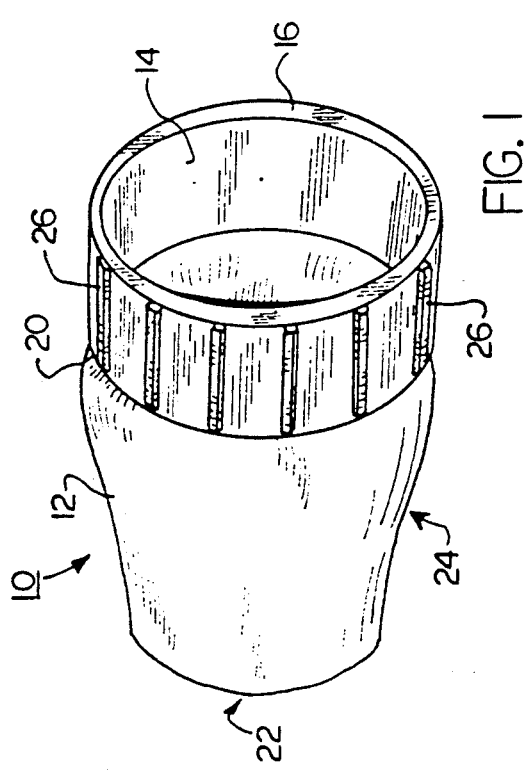
FIG. 1 is a perspective view of a prophylactic device constructed according to the present invention.

Referring now to the drawings in general and FIG. 1 in particular, it will be understood that the illustrations are for the purpose of describing a preferred embodiment of the invention and are not intended to limit the invention thereto. As best seen in FIG. 1, a prophylactic device, generally designated 10, is shown constructed according to the present invention. The device 10 includes two primary elements: an open ended sheath 12; and an elastic band 14.

Sheath 12 is attached at one end to either the edge 16 or, preferably, the rim 20 of band 14. A second opening 22 is at the end of sheath 12 opposite band 14. A neck portion 24 extends therebetween. Band 14 includes a series of longitudinal ribs 26 which assist in maintaining the band 14 around the neck of the penis without the band 14 becoming dislodged by rolling up upon itself. While the band 14 is elastic in nature, the material is soft and applies its elastic force gently without undue constriction. Use of the ribs 26 improves the anti-roll aspect which otherwise requires a slightly greater thickness to the band 14 than would be required if the ribs were included.

Figure 2:
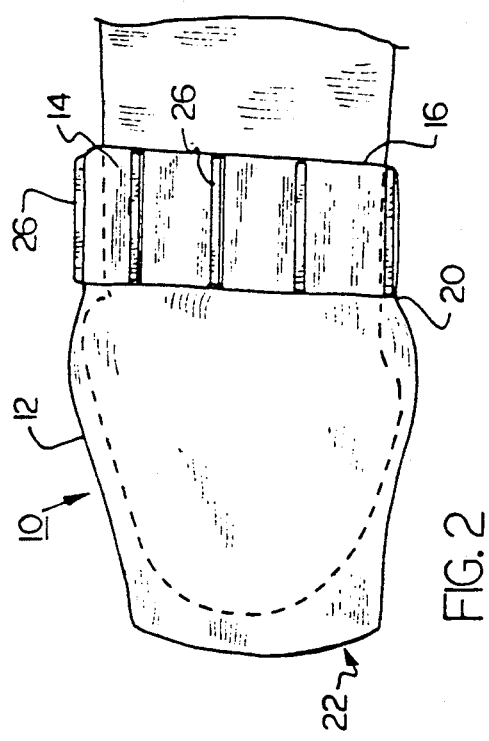
FIG. 2 is a generally schematic view of the device in its worn position.

Turning now to FIG. 2, there is shown a generally schematic view of the device in its worn position. Preferably the diameter of the second opening 22 is smaller than the diameter of the portion of the sheath 12 adjacent to band 14. Neck portion 24 is preferably bottleneck shaped, thereby generally following the contour of the glans penis. However, the diameter of the second opening 22 is of sufficient size to permit the sheath 12 to be retracted to permit normal micturition functions.

Figure 3:
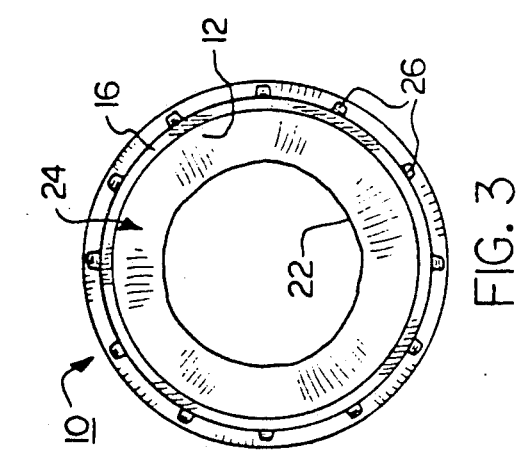
FIG. 3 is an end view of the device shown in FIG. 1.

As best seen in FIG. 3, an end view of the device shown in FIG. 1 is illustrated. The ribs 26 are generally uniformly arranged around the perimeter of the band 14.

Figure 4:
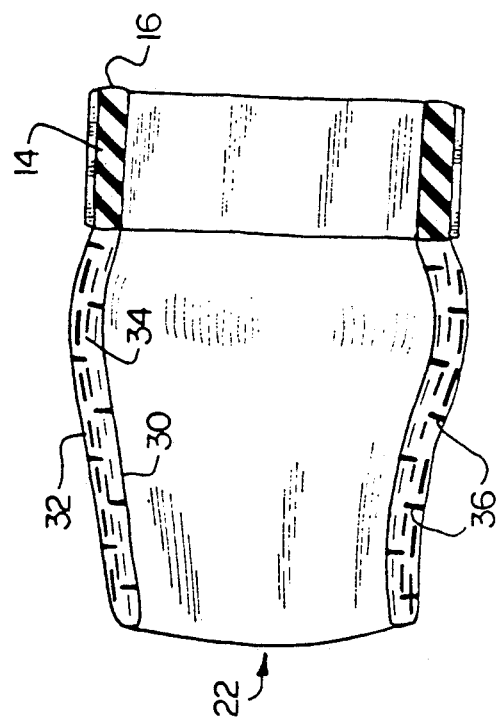
FIG. 4 is an enlarged vertical cross-sectional view of an alternative embodiment of the device shown in FIG. 1.

Finally, FIG. 4 shows an enlarged vertical cross-sectional view of an alternative embodiment of the device shown in FIG. 1. In the alternative embodiment, tubular sheath 12 is still open at both ends. However, sheath 12 has both an inner layer 30 and an outer layer 32. The use of two layers further reduce the transmission of tactile sensations through the sheath 14.

In the most preferred embodiment, inner layer 30 and outer layer 32 define a region therebetween for receiving a tactile preventing substance, such as a fluid 34. Any suitable material can be used to further limit the tactile contact between the glans and the clothing. However, silicon fluid is especially suitable since it is inert, harmless to the body, and available in a number of different viscosities. When a fluid is used, it may be advantageous to form a series of baffles 36 on the facing surfaces of inner wall 30 and outer wall 32 to slow the flow of the fluid 34, thereby further reducing any transmission of tactile sensations.

In both embodiments, the preferred sheath material is a soft latex or rubber material. The band should be easily stretchable such that the band is not unduly restricting if the male organ should become enlarged. The dimensions of the band are preferably 1/32 to 1/16 of an inch in thickness and ¼ to ½ inches in width. The circumference can vary in size but should be in the range of 3 to 4 inches to comfortably fit a pretumscent member. The ribs 26 may be used to retain the roll up prevention characteristics while minimizing the thickness of band 14.

Certain modifications and improvements will occur to those skilled in the art upon reading of the foregoing description. By way of example, an external lubricant could be added to the sheath to make it easier to pull on. Also, the sheath can be worn during sexual intercourse where it will function similarly to a natural foreskin by partially cover the head of the penis, thereby reducing contact and prolonging the act of intercourse. It should be understood that all such modifications and improvements have been deleted herein for the sake of conciseness and readability but are properly within the scope of the following claims.

I claim:

1. A prophylactic device worn on a penis, said device comprising:
   (a) a tubular sheath open at both ends; and
   (b) an elastic band attached along one of said ends of said sheath, said sheath and said band being constructed and sized to adapt to the distal end of said penis with said sheath extending substantially to only cover the glans of said penis and said band seating around the coronal sulcus of said penis to secure said device in position upon said penis, whereby said tubular sheath is operable to prevent contact between clothing and the glans of said penis while, at the same time, permitting normal micturition functions.

2. The device according to claim 1, wherein said sheath is bottle-shaped with the one of said ends of said sheath opposite said band being smaller in diameter than the other of said ends adjacent to said band.

3. The device according to claim 1, wherein said sheath and said band are of a unitary construction.

4. The device according to claim 1, wherein said band is relatively thick and wide to form a roll-preventing perimeter.

5. The device according to claim 4, wherein said band further includes raised, generally longitudinally extending ribs arranged about the outer surface of said band for preventing said band from rolling up.

6. A prophylactic device worn on a penis, said device comprising:
   (a) a tubular sheath open at both ends, said sheath having an inner layer and an outer layer defining a region therebetween for receiving a tactile preventing substance; and
   (b) an elastic band attached along one of said ends of said sheath, said sheath and said band being constructed and sized to adapt to the distal end of said penis with said sheath extending substantially to only cover the glans of said penis and said band seating around the coronal sulcus of said penis to secure said device in position upon said penis, whereby said tubular sheath is operable to prevent contact between clothing and the glans of said penis while, at the same time, permitting normal micturition functions.

7. The device according to claim 6, wherein said tactile preventing substance is a liquid.

8. The device according to claim 7, wherein at least one of said inner layer and said outer layer defining a region therebetween includes a series of parallel baffles along its inner surface for slowing the flow of said tactile preventing liquid.

9. The device according to claim 6, wherein said sheath is bottle-shaped with the one of said ends of said sheath opposite said band being smaller in diameter than the other of said ends adjacent to said band.

10. The device according to claim 6, wherein said sheath and said band are of a unitary construction.

11. The device according to claim 6, wherein said band is relatively thick and wide to form a roll-preventing perimeter.

12. The device according to claim 11, wherein said band further includes raised, generally longitudinally extending ribs arranged about the outer surface of said band for preventing said band from rolling up.

* * * * *